(12) United States Patent
Rozas et al.

(10) Patent No.: US 8,690,745 B2
(45) Date of Patent: Apr. 8, 2014

(54) FLUID TRANSFER FOR RADIATION TREATMENT APPARATUS

(75) Inventors: David Rozas, Waltham, MA (US); John Dobbs, Beverly, MA (US); Robert F. Riemer, Andover, MA (US); Daniel Abenaim, Lynnfield, MA (US)

(73) Assignee: Analogic Corporation, Peabody, MA (US)

( * ) Notice: Subject to any disclaimer, the term of this patent is extended or adjusted under 35 U.S.C. 154(b) by 543 days.

(21) Appl. No.: 13/015,965

(22) Filed: Jan. 28, 2011

(65) Prior Publication Data
US 2011/0124946 A1    May 26, 2011

Related U.S. Application Data

(63) Continuation of application No. PCT/US2008/071760, filed on Jul. 31, 2008.

(51) Int. Cl.
*A61N 5/01* (2006.01)

(52) U.S. Cl.
USPC .................................. 600/1; 378/21

(58) Field of Classification Search
USPC ........ 600/1; 378/21, 145, 147, 148, 149, 199, 378/200
See application file for complete search history.

(56) References Cited

U.S. PATENT DOCUMENTS

| | | | |
|---|---|---|---|
| 4,928,283 A | 5/1990 | Gordon | |
| 5,037,374 A | 8/1991 | Carol | |
| 5,110,159 A | 5/1992 | Herold et al. | |
| 5,442,675 A | 8/1995 | Swerdloff et al. | |
| 5,518,693 A | 5/1996 | Tomasso et al. | |
| 5,732,123 A | 3/1998 | Peralta et al. | |
| 6,412,979 B1 * | 7/2002 | Hell et al. | 378/200 |
| 2004/0109538 A1 | 6/2004 | Joseph, Jr. | |
| 2004/0202287 A1 | 10/2004 | Muller | |
| 2004/0228450 A1 | 11/2004 | Mueller | |
| 2006/0215808 A1 | 9/2006 | Lacey | |
| 2007/0069406 A1 * | 3/2007 | Phouybanhdyt et al. | 261/153 |

OTHER PUBLICATIONS

International Search Report in related application No. PCT/US2008/071760 dated Jun. 9, 2009.

* cited by examiner

*Primary Examiner* — Christine Matthews
*Assistant Examiner* — Joshua D Lannu
(74) *Attorney, Agent, or Firm* — Cooper Legal Group LLC (57) ABSTRACT

Techniques and systems for supplying fluid to a rotating gantry portion of a radiation treatment apparatus are disclosed where a first batch fluid is supplied to the rotating gantry when the rotating gantry is stationary a first time, discontinuing the supply when the rotating gantry is rotating, and supplying a second batch of fluid when the rotating gantry is stationary a second time. A storage component on the rotating gantry allows supplied fluid to be stored in the rotating gantry and used to shape a radiation beam and/or cool an ionizing radiation source, for example, while the rotating gantry is rotating. The techniques and systems may also be utilized to discharge a first fluid from the rotating gantry and supply a second fluid to replace the first fluid.

31 Claims, 7 Drawing Sheets

FLUID TRANSFER FOR RADIATION TREATMENT APPARATUS

RELATED APPLICATIONS

This application is a continuation of PCT/US2008/071760 filed Jul. 31, 2008, the contents of which are incorporated by reference herein.

BACKGROUND

The present application applies to fluid transfer in radiation treatment equipment, and particularly to the transfer of compressed air and/or other fluids to the moving portions of such equipment. While it finds particular application to radiation treatment equipment for use in medicine, it also relates to other applications in which a fluid is supplied to a moving portion of a treatment device.

Radiation treatment, in general, is the use of ionizing radiation for the treatment of an object. In medicine, radiation treatment is commonly used in the treatment of cancer and other disease. To this end, it is generally desirable to apply a desired radiation dose or dose distribution to a tumor or other region to be treated, while minimizing the dose supplied to healthy tissues.

One type of radiation treatment apparatus is described in U.S. Pat. No. 5,442,675 by Swerdloff et al. More particularly, a linear accelerator, and collimator are mounted to a rotating gantry. As the gantry rotates about a patient, a pneumatic actuator is used to vary the collimator and thus modulate the shape of the radiation beam applied to the patient from each of a plurality of angles or projections about the patient.

Compressed gas for operating the actuator is supplied to the rotating gantry via an airtight rotating union having roughly the same circumference as the rotating gantry. Thus, as the rotating gantry rotates about the patient, compressed air supplied through the rotating union is used to operate the actuator and hence vary the shape of the radiation beam applied to the patient.

While such a configuration has proven effective in practical treatment systems, there remains room for improvement. For example, the rotating unions can be relatively difficult to manufacture, and their reliability can be deleteriously affected by factors such as mechanical wear.

Another consideration is the delivery of a coolant that serves to cool the linear accelerator. To this end, the rotating gantry has included a closed loop cooling system. Unfortunately, however, the coolant must be changed or flushed from time to time to, among other things, remove particulate matter that may accumulate during use. Since the cooling system is integrated within the rotating gantry, however, a service technician has to be engaged to disassemble the scanner, flush the fluid and then reassemble the scanner—a time consuming, labor intensive, and therefore expensive proposition.

SUMMARY

Aspects of the present application address the above matters, and others. According to a first aspect, a radiation treatment apparatus includes a stationary gantry portion and a rotating gantry portion configured to rotate relative to the stationary gantry portion. The rotating gantry portion is configured to receive a fluid during a time in which the rotating gantry portion is stationary with respect to the stationary gantry portion and to discontinue the supply of the fluid while the rotating gantry portion is rotating relative to the stationary portion. The apparatus also includes an ionizing radiation source carried by the rotating gantry portion.

According to another aspect, a radiation treatment apparatus includes a stationary portion, a rotating portion configured to intermittently rotate about an object relative to the stationary portion, and a transfer component. The transfer component is comprised within the stationary portion and configured to transfer fluid to the rotating portion when the rotating portion is stationary and to discontinue the transfer when the rotating portion is rotating.

According to another aspect, a method for use with a radiation therapy apparatus that comprises a stator, a rotor, and a radiation source carried by the rotor for applying an ionizing radiation to an object to be treated is provided. The method includes supplying a first fluid to the rotor during a time in which the rotor is stationary with respect to the stator. The method also includes discontinuing the supply of the first fluid to the rotor, rotating the rotor with respect to the stator, using the supplied fluid to perform a function of the apparatus during a time in which the rotor is rotating with respect to the stator, and repeating one or more of the acts of supplying, discontinuing, rotating, and supplying.

Those of ordinary skill in the art will appreciate still other aspects of the present application upon reading and understanding the following description.

DETAILED DESCRIPTION

The claimed subject matter is now described with reference to the drawings, wherein like reference numerals are used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

Figure 1:
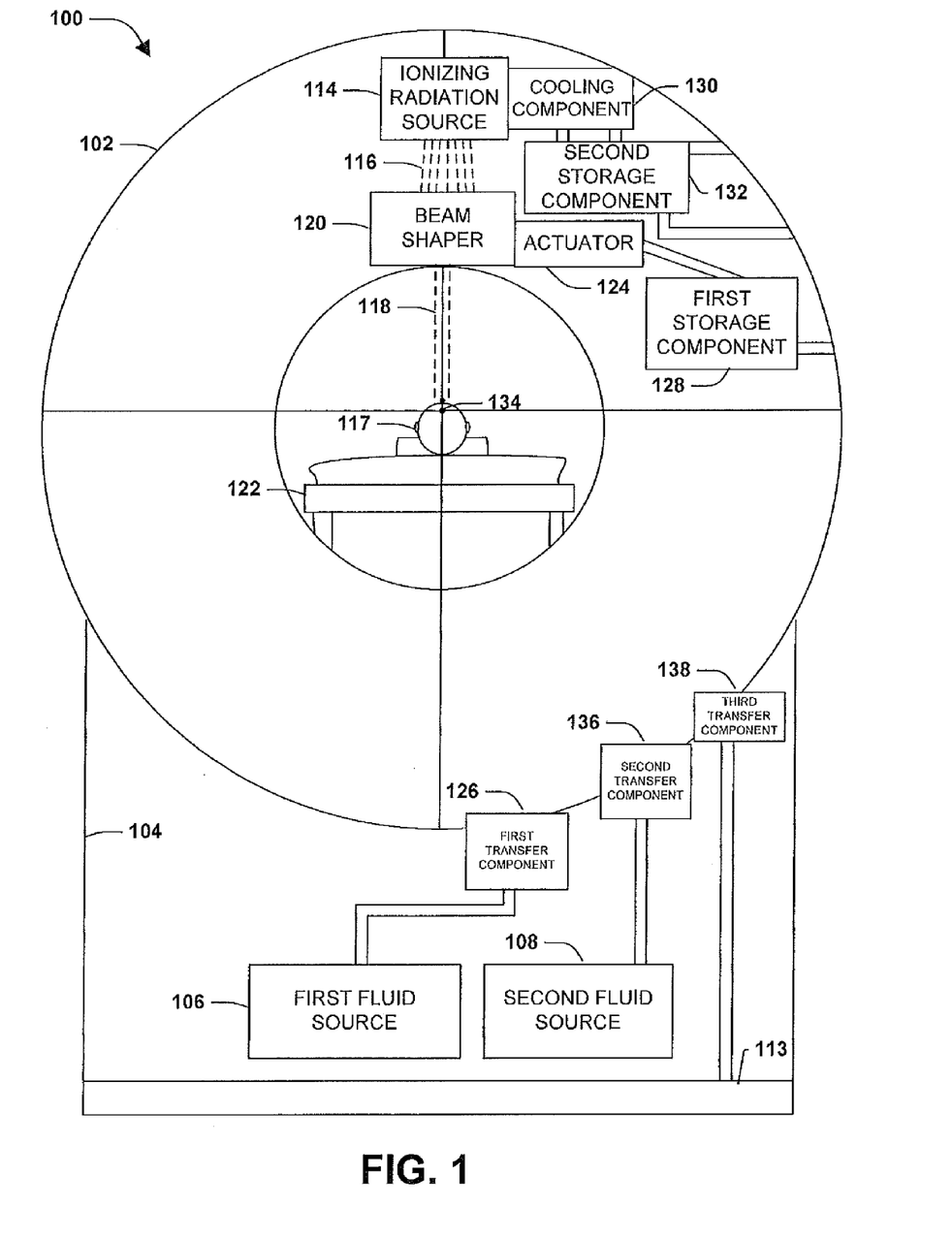
FIG. 1 depicts a radiation treatment apparatus.

FIG. 1 depicts a radiation treatment apparatus 100. As illustrated, the apparatus 100 includes an object support 122 configured to support a human patient or other object 117 to be treated, a generally stationary gantry portion 104, and a rotating gantry portion 102 configured for rotation relative to the stationary gantry portion 104 about an axis of rotation 134. It will be understood that the stationary gantry portion 104 need not be perfectly stationary and may, for example, be configured to translate along the axis of rotation 134, or the like. In the illustrated implementation, the rotating gantry 102 defines a generally cylindrical bore having a diameter sized to receive the head, body, or other desired portion of a human patient. In a whole body application, for example, the bore may have an outer diameter of roughly one meter, although other sizes and configurations are contemplated.

The rotating gantry 102 includes an ionizing radiation source 114, a beam shaper 120, a pneumatic actuator 124, and a first storage component 128. The pneumatic actuator 124 could be external to or integrated within the beam shaper 120. The ionizing radiation source 114 may include an x-ray tube, linear accelerator, radionuclide, proton source, or other suitable source of ionizing radiation. In medicine, the ionizing radiation source 114 produces radiation 116 that may be directed towards a treatment region on an object 117. The rotating gantry 102 and the ionizing radiation source 114 rotate about the object 117.

The radiation 116 is designed to destroy cells, for example, in the treatment region. In order to create a dose profile which is conformal with the target treatment volume while limiting the dose to healthy tissue, radiation 116 is passed through the beam shaper (e.g., a multi-leaf collimator) 120 which shapes radiation into a beam 118 in coordination with the rotation of the gantry about treatment region.

The beam shaper 120 varies the shape, intensity, or other characteristic of the radiation 116 from the radiation source 114 for application to the object 117 (e.g., providing a desired dose distribution to the object 117). More particularly, the pneumatic actuator 124 varies the beam shaper 120 so as to vary the characteristic of the radiation 116 applied to the object 117 in coordination with the rotation of the rotating gantry 102 about the axis of rotation 134. Where the beam shaper 120 includes a multi leaf collimator, for example, the beam shaper 120 may be configured to vary the positions of the various collimator leaves.

As provided herein, the fluid used by the actuator 124 may be supplied to the rotating gantry 102 through a first transfer component 126 when the rotating gantry 102 is in a stationary position. The fluid may be stored in the first storage component 128, then used to drive the actuator 124 when the rotating gantry 102 is rotating relative to the stationary gantry 104. This allows the rotating gantry 102 the flexibility of rotating freely without the use of a rotating union for supplying the fluid, for example.

The first storage component 128 includes a reservoir for storing compressed air or other fluid. The first storage component 128 is pneumatically connected (or otherwise in operative fluid communication) with a mechanism that uses the fluid, such as the actuator 124, so as to supply the mechanism while the rotating gantry 102 rotates about the object 117. Hence, in the case of a pneumatic actuator 124, compressed air from the first storage component 128 provides motive force for varying the position of the actuator 124 and hence the characteristic of the radiation 116 applied to the object 117.

With further reference to FIG. 1, the stationary gantry 104 also includes a first fluid source 106. Again in the example of a treatment apparatus 100 that includes a pneumatic actuator 124, the first fluid source 106 may include an air or other compressor, a compressed gas tank, or the like.

It will be appreciated that the ionizing radiation source 114 uses a cooling component 130 (e.g., a heat exchanger) to inhibit the ionizing radiation source 114 from overheating. In one example, the cooling component 130 passes relatively cool fluid (e.g., through a closed loop) from a second storage component 132 into the ionizing radiation source 114. Heat is absorbed into the fluid while it is in the ionizing radiation source 114, and the fluid is passed back to the cooling component 130 wherein the heat is extracted before the fluid reenters the second storage component 132.

Periodically, the fluid is flushed to prevent an excessive amount of particulates and/or contaminates, for example, from building up in the closed loop. A second transfer component 136 provides a means for supplying fluid to the second storage component 132 from a second fluid source 108 and a third transfer component 138 allows fluid already in the second storage component 132 to exit the rotating gantry 102 when it is in a stationary position. It will be appreciated that in one embodiment, the third transfer component 138 is omitted and replaced by another mechanism, such as a valve, petcock, or vent, wherein gravity causes the fluid to drain out of the rotating gantry 102. The fluid that exits the rotating gantry 102 may be transferred to a drain pan 113 and/or a drain, such as illustrated in FIG. 1.

Figure 2:
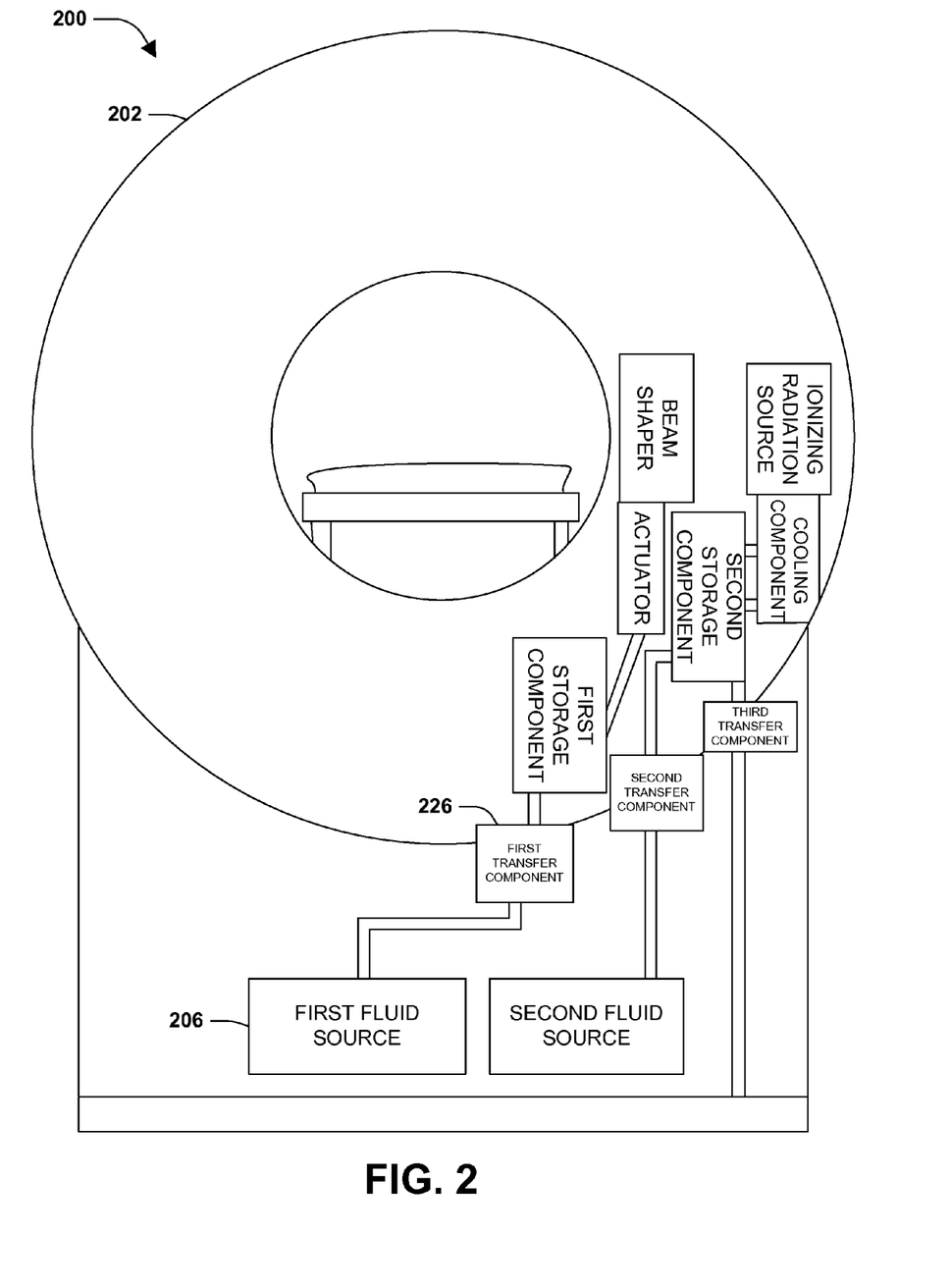
FIG. 2 depicts the rotating portion of a radiation treatment apparatus in a parked position.

By way of example, FIGS. 2-8 illustrate example environments for supplying fluid to a rotating gantry when the rotating gantry is stationary and discontinuing the supply when the rotating gantry is rotating. More particularly, FIGS. 2-8 illustrate ways of supplying fluid to a first storage component that is comprised in and/or on the rotating gantry. FIG. 2 illustrates a radiation treatment apparatus 200 (e.g., 100 in FIG. 1) wherein a rotating gantry 202 (e.g., 102 in FIG. 1) is stationary and/or has rotated to a parked position (e.g., the radiation treatment apparatus 200 is not being used to treat an object). The parked position may be defined as a predetermined rotational angle that the rotating gantry 202 intermittently returns to when it is not rotating. Once the rotating gantry 202 is stationary, fluid is supplied to it via a first fluid source 206 (e.g., 106 in FIG. 1), for example. In one example, the rotating gantry 202 may be locked in place to prevent it from rotating while it is receiving fluid. It will be understood by those of ordinary skill in the art that the rotating gantry 202 may be supplied with fluid at a different position, and/or it may be supplied at different positions at different instances. For example, a user may connect a hose to the rotating gantry 202 wherever the portion of a first transfer component 226 (e.g., 126 in FIG. 1) affixed to the rotating gantry 202 stops, thereby not being in a predetermined parked position.

Figure 3:
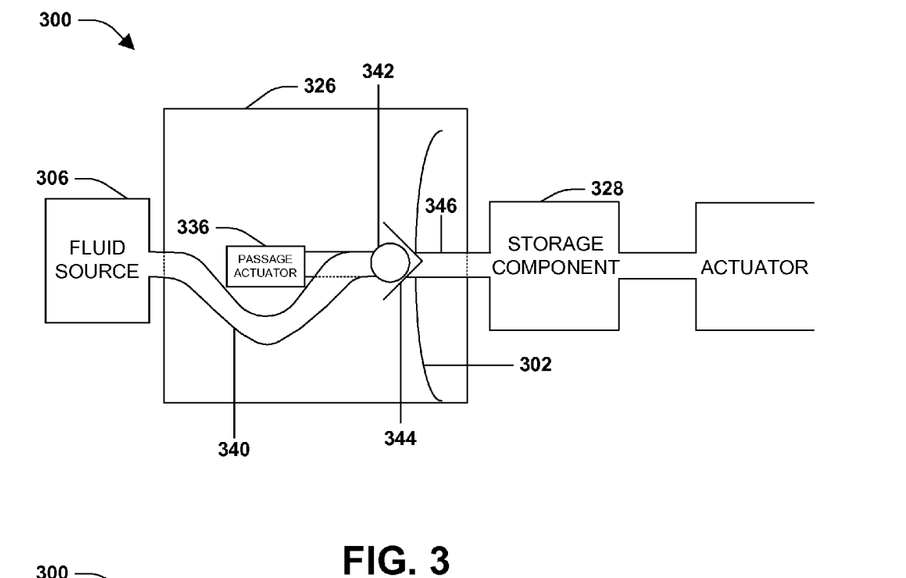
FIG. 3 is a schematic block diagram illustrating one or more components of an environment wherein fluid may be supplied to a rotating portion of a radiation treatment apparatus when it is stationary.

FIG. 3 illustrates one or more components of an exemplary environment 300 wherein fluid may be received by a rotating gantry 302 (e.g., 202 in FIG. 2) when it is in a stationary position. More particularly, FIG. 3 illustrates the rotating gantry 302, a fluid source 306 (e.g., 206 in FIG. 2) configured to supply fluid, a transfer component 326 (e.g., 226 in FIG. 2), and a storage component 328 (e.g., 128 in FIG. 1). The transfer component 326 comprises a passage actuator 336, a first fluid passage 340 (e.g., a hose), a male coupler 342, a second fluid passage 346, and a female coupler 344 configured to couple with the male coupler 342. In one example, the male and female couplers, 342 and 344, are quick-connect couplers (e.g., allowing the couplers to be easily coupled and decoupled). Quick-connect couplers may be defined as self-sealing (e.g., using an annular electrostatic seal) connecting devices that include an internal check valve (e.g., poppet valves, stopcock valves, etc.). Quick-connect couplers generally couple, seal, and/or decouple as a result of axial motion. A single-point attachment, push-to-connect/pull-to-disconnect coupler, for example, is a basic type of quick-connect coupler.

Fluid may be transferred to the rotating gantry 302 once it is stationary. To transfer fluid, the passage actuator 336 (e.g., pneumatic, hydraulic, gear driven, etc.) extends the first fluid passage 340 so that the male coupler 342 is coupled to the female coupler 344 affixed to the rotating gantry 302. Once the couplers, 342 and 344, are coupled, fluid may pass from the fluid source 306 (e.g., an air compressor, a tank, etc.) to the storage component 328 on the rotating gantry 302 via the first and second fluid passages, 340 and 346.

It will be appreciated to those of ordinary skill in the art that various other configurations for supplying fluid to the rotating gantry 302 on a radiation treatment apparatus have been contemplated. In one example, the placement of the male and female couplers, 342 and 344, are reversed. In another example, the fluid source 306 is attached to a structure (e.g., a wall) outside the radiation treatment apparatus and a user extends a fluid passage from a service loop (e.g., also attached to the wall) and connects the male coupler 342 to the female coupler 344. In yet another example, the passage actuator 336 is on the rotating gantry and extends the second fluid passage 346 (e.g., the first fluid passage 340 is stationary).

Figure 4:
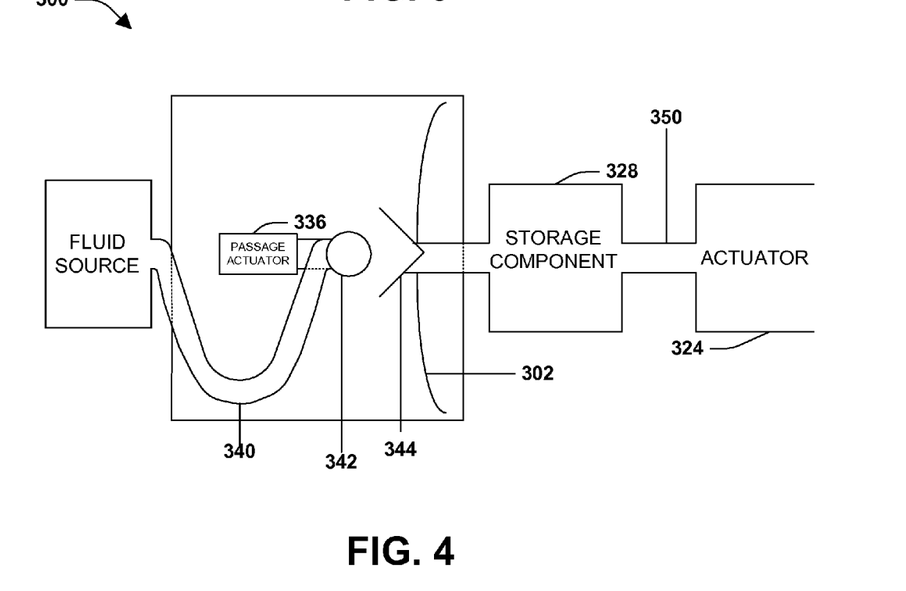
FIG. 4 is a schematic block diagram illustrating one or more components of an environment wherein fluid may not be supplied to a rotating portion of a radiation treatment apparatus when it is rotating.

FIG. 4 illustrates the example environment 300, after the storage component 328 has a predetermined amount of fluid added thereto and/or the rotating gantry 302 is preparing to rotate (e.g., to provide radiation). In the illustrated example, the passage actuator 336 retracts the first fluid passage 340 causing the male coupler 342 and the female coupler 344 to decouple. The first fluid passage 340 may be made of a material that expands and/or contracts (e.g., in an accordion like manner) and/or made of a more rigid material wherein the first fluid passage 340 hangs down when it is retracted. It will be appreciated that the rotating gantry 302 may have a locking apparatus on it to prevent it from rotating prior to the passage actuator 336 retracting the first fluid passage 340 (e.g., so that the first fluid passage 340 and/or the rotating gantry 302 are not damaged by a rotation while the male and female couplers, 342 and 344, are coupled).

While the radiation treatment apparatus is in use (e.g., the rotating gantry 302 is rotating), the storage component 328 supplies fluid to an actuator 324 (e.g., 124 in FIG. 1), for example, via a third fluid passage 350. When the radiation treatment apparatus has finished its treatment and/or the fluid in the storage component 328 is less than some predetermined threshold, the rotating gantry 302 may return to its parked position (e.g., as illustrated in FIG. 2) and the storage component 328 on the rotating gantry 302 may be refilled with fluid (as illustrated in FIGS. 3-4). It will be appreciated that the storage component 328 may have a detection component configured to determine when the fluid is below a predetermined threshold. It will also be appreciated that an indicator light, alarm, etc. on the radiation treatment apparatus may indicate when the rotating gantry 302 should receive more fluid (e.g., because the amount of fluid in the storage component 328 falls below some predetermined threshold). While this environment 300 illustrates the fluid flowing to the actuator 324, it will be understood that the fluid may be supplied to other components of the rotating gantry 302, such as a cooling component, for example.

Figure 5:
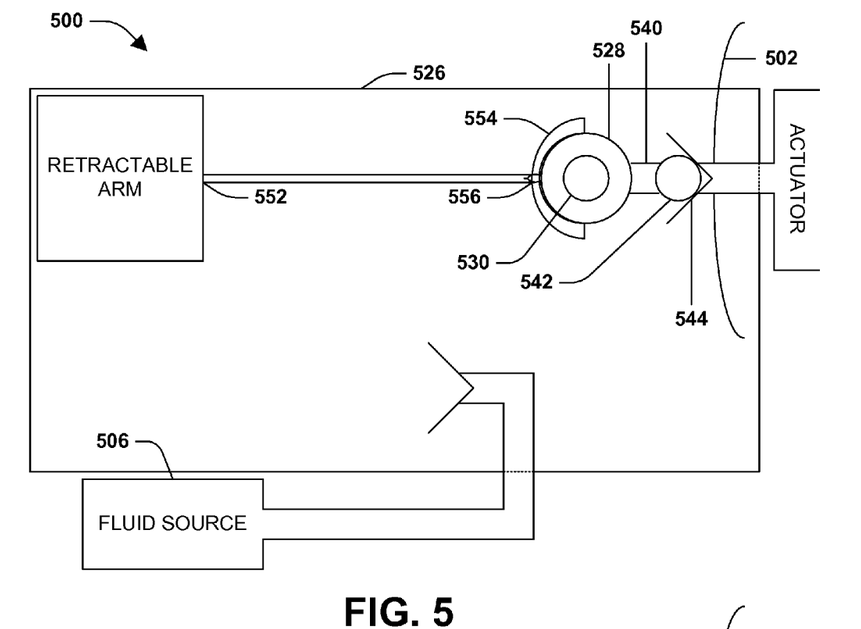
FIG. 5 is a schematic block diagram illustrating one or more components of an environment wherein fluid may be supplied to an interchangeable storage component on a rotating portion of a radiation treatment apparatus when it is stationary.

FIG. 5 illustrates one or more components of an exemplary environment 500 wherein fluid may be received by a rotating gantry 502 (e.g., 202 in FIG. 2) when it is in a stationary position. More particularly, FIG. 5 illustrates the rotating gantry 502, a fluid source 506 (e.g., 206 in FIG. 2) configured to supply fluid, a transfer component 526 (e.g., 226 in FIG. 2), and an interchangeable storage component 528 (e.g., 128 in FIG. 1). The transfer component 526 comprises a retractable arm 552 configured to extend and/or retract and/or move side-to-side, grippers 554 configured to grip the interchangeable storage component 528, a hinge 556 configured to open and/or close the grippers 554, and a first female coupler 544 (e.g., 344 in FIG. 3). The interchangeable storage component 528 comprises a storage compartment 530 configured to store fluid, a first fluid passage 540, and a male coupler 542 (e.g., 342 in FIG. 3) configured to couple to the first female coupler 544. In one example, the male and first female couplers, 542 and 544, are quick-connect couplers, allowing the couplers to be easily coupled and decoupled. It will be appreciated that other types of couplers, such as threaded couplers (e.g., similar to those commonly found on garden hoses), are also contemplated.

In FIG. 5, the retractable arm 552 is extended (e.g., using gears, hydraulics, etc.) to retrieve the interchangeable storage component 528. The hinge 556 (which may be hydraulically and/or manually controlled) opens the grippers 554 so that they fit around the outside of the interchangeable storage component 528. Once the grippers 554 are around the interchangeable storage component 528, the hinge 556 closes so that the grippers 554 are gripping the interchangeable storage component 528. In the illustrated example, the interchangeable storage component 528 is cylindrical and the grippers 554 act as an arcuate claw that surrounds a portion of the cylinder. It will be appreciated that multiple other shapes and or configurations for the interchangeable storage component 528 and grippers 554 are contemplated. In one example, the grippes 554 are a suction apparatus that suctions to (the bottom of) the interchangeable storage component 528.

Figure 6:
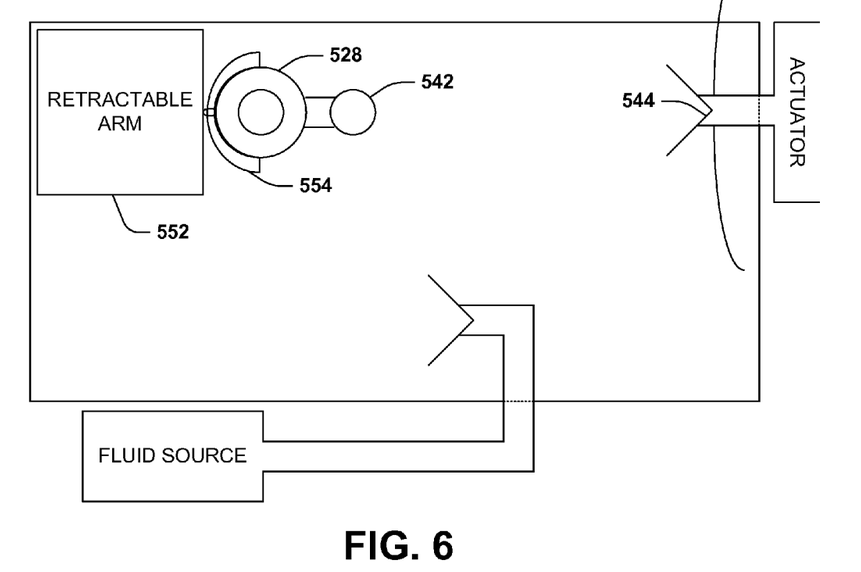
FIG. 6 is a schematic block diagram illustrating one or more components of an environment wherein an interchangeable storage component is decoupled from a rotating portion of a radiation treatment apparatus.

After the grippers 554 grip the interchangeable storage component 528, the retractable arm 552 retracts, causing the male coupler 542 to decouple from the first female coupler 544. As illustrated in FIG. 6, the retractable arm 552 continues to retract the interchangeable storage component 528 until it is retracted some predetermined amount/distance.

Figure 7:
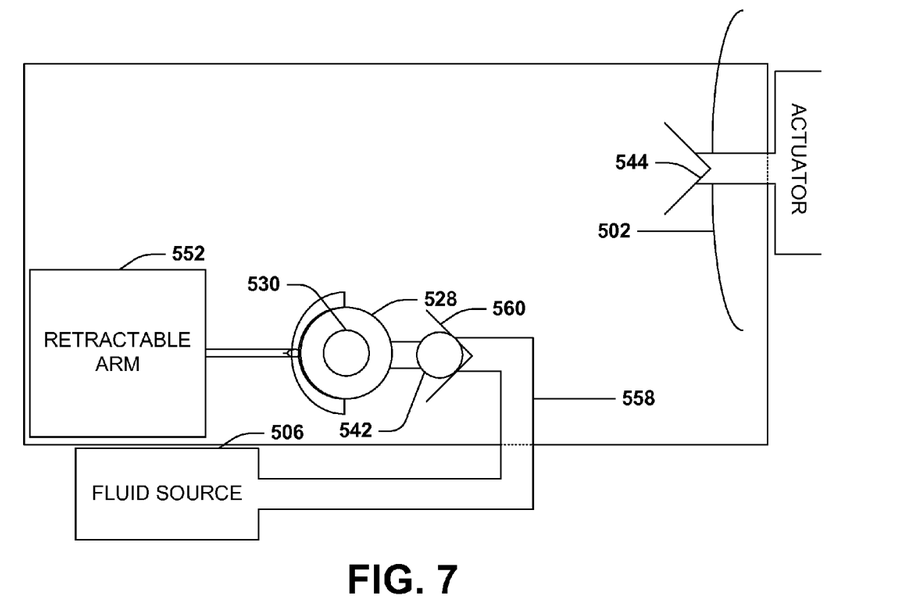
FIG. 7 is a schematic block diagram illustrating one or more components of an environment, wherein an interchangeable storage component is filled with fluid.

In FIG. 7, the retractable arm 552 is placed under a second female coupler 560 that is attached to a second fluid passage 558. In one example, the retractable arm 552 has small wheels that allow it to slide along a track that extends under/to the second female coupler 560. In another example, the retractable arm 552 is stationary and the second female coupler 560 moves to a location aligned with/directly above the male coupler 542. Once the retractable arm 552 is aligned with the second female coupler 560, the retractable arm 552 is extended so that the male coupler 542 is coupled to the second female coupler 560. Fluid is then passed from the fluid source 506 to the storage compartment 530 in the interchangeable storage component 528.

Once the storage compartment 530 has a predetermined amount of fluid and/or the rotating gantry 502 prepares to move, the retractable arm 552 retracts, causing the male and second female couplers, 542 and 560, to decouple from one another. The retractable arm 552 is then (re)aligned with the first female coupler 544. Once the male coupler 542 and the first female coupler 544 are aligned, the retractable arm is extended to allow the male coupler 542 and the first female coupler 544 to recouple.

Figure 8:
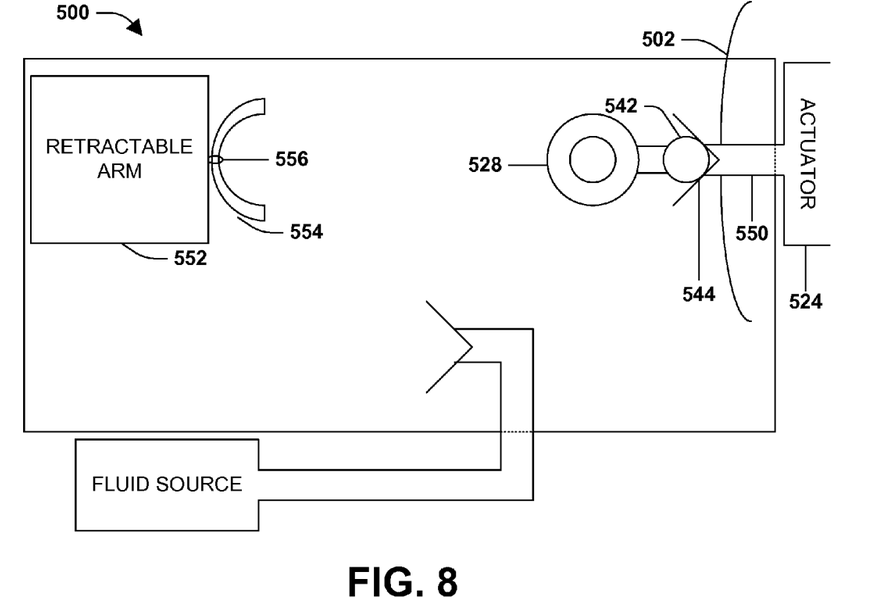
FIG. 8 is a schematic block diagram illustrating one or more components of an environment, wherein an interchangeable storage component is recoupled to a rotating portion of a radiation treatment apparatus.

In FIG. 8, the hinge 556 is opened and the grippers 554 release the interchangeable storage component 528. The interchangeable storage component 528 is held to the rotating gantry 502 by the coupling of the male coupler 542 and first female coupler 544. It will be appreciated that a strap and/or some other apparatus may be used to further support the interchangeable storage component 528 (e.g., such as when it is too heavy to be supported by the male and first female couplers, 542 and 544).

Once the retractable arm 552 is retracted, the rotating gantry 502 may begin to rotate. It will be appreciated that the rotating gantry 502 may have a locking apparatus on it to prevent it from rotating prior to the retractable arm 552 being retracted (e.g., so that the retractable arm 552, the interchangeable storage component 528 and/or the rotating gantry 502 are not damaged while the interchangeable storage component 528 is being transferred).

While the radiation treatment apparatus is in use (e.g., the rotating gantry 502 is rotating), the interchangeable storage component 528 supplies fluid to an actuator 524 (e.g., 124 in FIG. 1), for example, via a third fluid passage 550. When the radiation treatment apparatus has finished its treatment and/or the fluid in the interchangeable storage component 528 is less than some predetermined threshold, the rotating gantry 502 may return to a stationary and/or parked position (e.g., similar to that illustrated in FIG. 2) and the interchangeable storage component 528 may be refilled with fluid (as illustrated in FIGS. 5-8). It will be appreciated that the interchangeable storage component 528 may have a detection component configured to determine when the fluid is less than a predetermined threshold. It will also be appreciated that an indicator light, alarm, etc. on the radiation treatment apparatus may indicate when the rotating gantry 502 should return to the parked position to receive more fluid. While this environment 500 illustrates the fluid flowing to the actuator 524, it will be understood that the fluid may be supplied to other components of the rotating gantry 502, such as a cooling component, for example.

Environment 500, as illustrated in FIGS. 5-8, may be automated and or manually driven. For example, the transfer component 526 may not use a retractable arm 552, and the interchangeable storage component 528 may be coupled and/or decoupled by a user. In another example, the transfer component 526 is included in a stationary gantry (e.g., 204 of FIG. 2) and the environment is automated using computer controlled hydraulics.

In one embodiment, multiple interchangeable storage components (e.g., similar to 528 in FIG. 5) may be used to supply a rotating gantry (similar to 502 in FIG. 5) with fluid. For example, multiple storage components may be coupled to the rotating gantry at once via multiple female couplers on the rotating gantry. Additionally, some interchangeable storage components may be stored in a stationary gantry (similar to 104 in FIG. 1). In one example, a first interchangeable storage component is replaced with a second interchangeable storage component when the fluid in the first interchangeable storage component falls below a predetermined threshold. The first interchangeable component (now decoupled from the gantry) could then be refilled, for example, while the rotating gantry is using fluid from the second interchangeable storage component. Having multiple interchangeable storage components would allow the rotating gantry to remain stationary for less time (e.g., by not having to remain stationary while one or more "empty" interchangeable storage component are refilled) and/or allow the rotating gantry to rotate for a longer period of time before returning for additional fluid (e.g., where multiple interchangeable storage components are coupled to the rotating gantry at once).

Figures 9, 10:
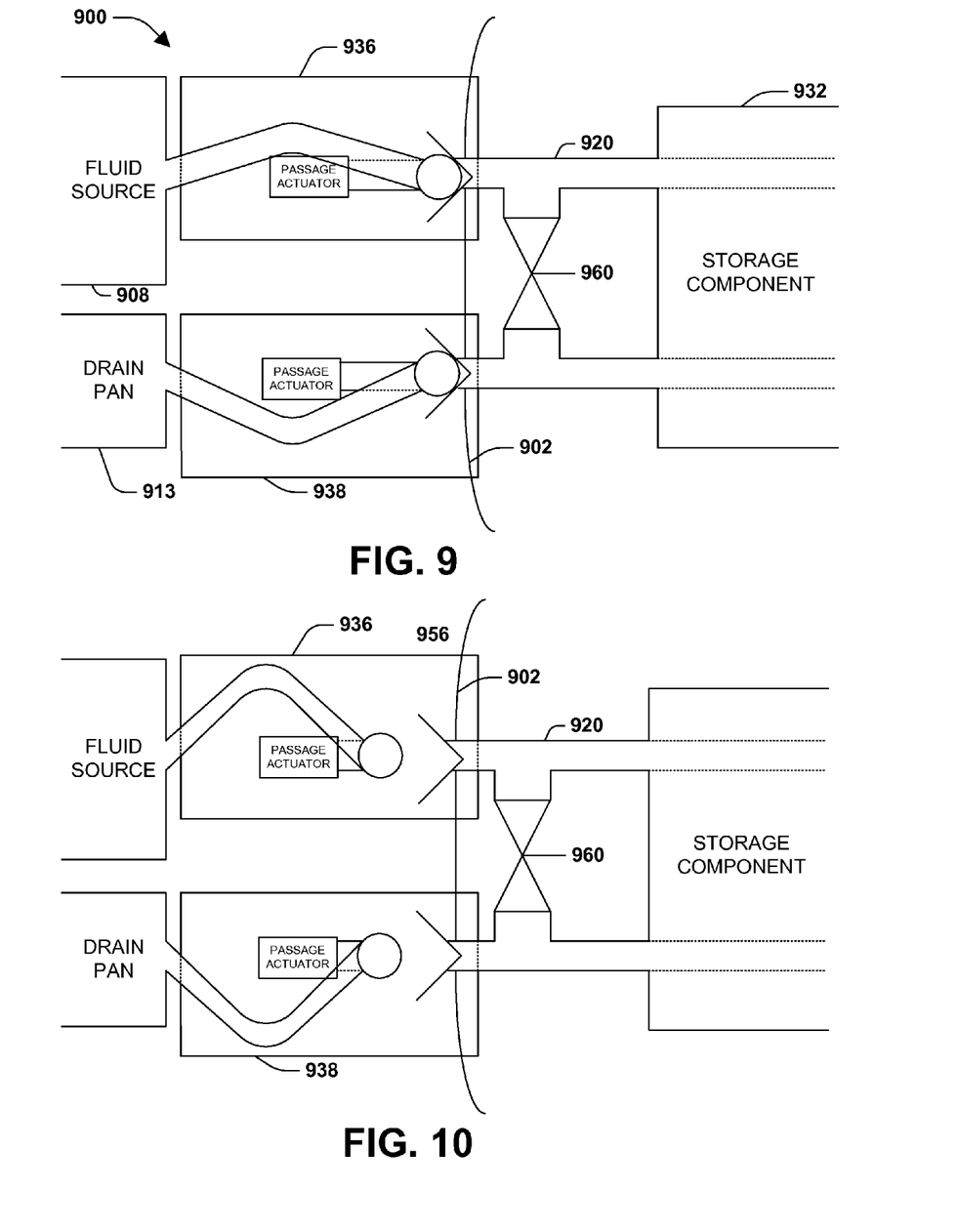
FIG. 9 is a schematic block diagram illustrating one or more components of an environment wherein fluid may be flushed from a rotating portion of a radiation treatment apparatus when it is stationary.
FIG. 10 is a schematic block diagram illustrating one or more components of an environment wherein fluid may not be flushed from a rotating portion of a radiation treatment apparatus when it is rotating.

FIGS. 9-10 illustrate an example environment for flushing a fluid from a rotating gantry when the rotating gantry is stationary and discontinuing the flush when the rotating gantry is rotating (e.g., as discussed above with reference to FIG. 1). Those of ordinary skill in the art will understand that multiple other configurations and/or apparatuses (e.g., besides those illustrated herein) for flushing a fluid in a rotating gantry are contemplated.

FIG. 9 illustrates one or more components of an exemplary environment 900 for flushing a fluid from a storage component 932 (e.g., 132 in FIG. 1). In the illustrated example, a rotating gantry 902 (e.g., 202 in FIG. 2) is stationary. A second transfer component 936 (e.g., 136 in FIG. 1) allows a second fluid to pass from a fluid source 908 (e.g., 108 in FIG. 1) to the storage component 932 when the rotating gantry 902 is not rotating. It will be appreciated that the second transfer component 936 may operate in a manner similar to that described with regards to environment 300 (e.g., using quick-connect couplers).

As the second fluid enters the storage component 932, a first fluid, already in the storage component 932, may exit the storage component 932 through a third transfer component 938 (e.g., 138 in FIG. 1) and flow into a drain pan 913 (e.g., 113 in FIG. 1). It will be appreciated that the third transfer component 938 may operate in a manner similar to that describe with regards to environment 300 (e.g., a passage actuator may cause a male coupler to connect to a female coupler affixed to the rotating gantry 902). It will be appreciated that unlike the transfer component 326 of environment 300, the third transfer component 938 acts as an output, allowing fluid to flow out of the rotating gantry 902 (e.g., whereas the transfer component 326 and the second transfer component 926 are inputs, allowing fluid to flow into rotating gantry). To ensure that the first fluid does not remain in a closed loop 920 (e.g., between the storage component 932, a cooling component, and an ionizing radiation source), a valve 960, and/or some other mechanism that prevents fluid from flowing through a portion of the closed loop, may be placed between the portions of the second and third transfer components, 936 and 938, attached to the rotating gantry 902.

As illustrated in FIG. 10, the portion of the second and third transfer components, 936 and 938, not affixed to the rotating gantry 902 retract, after the first fluid has been flushed and/or the rotating gantry 902 prepares to rotate. Similar to that described in environment 300, fluid passages are retracted and couplers are decoupled. The valve 960 also opens, allowing fluid to flow through the closed loop 920. After a predetermined amount of uses and/or according to some other predetermined criteria, the rotating gantry 902 may be flushed again.

To maintain the radiation treatment apparatus in a desired condition, for example, the apparatus may have a detection component on it to indicate when a fluid should be flushed.

Additionally, similarly to environment 300 in FIG. 3, environment 900 may be automated and/or manually actuated by a user/service professional.

It will be appreciated that while example environment 900 illustrates a second fluid pushing the first fluid out of the closed loop 920, the first fluid may exit the rotating gantry 902 before the second fluid enters the rotating gantry 902. For example, the drain pan 913 may contain a pump that causes the first fluid to be pulled (e.g., via vacuum) out of the rotating gantry. Additionally, a valve or petcock may be used and the first fluid may drain out as a result of gravity. In another example, the second transfer component 936 provides a means for the first fluid to exit the rotating gantry 902, and, once the first fluid is out of the rotating gantry 902, the second transfer component 936 provides a means for the second fluid to enter the rotating gantry 902. In yet another example, two interchangeable storage components (e.g., similar to 528 in FIG. 5) may be attached to the rotating gantry 902 wherein fluid from one interchangeable storage component pushes the fluid already in the rotating gantry 902 out of the closed loop 920 and into a second interchangeable storage component.

Figure 11:
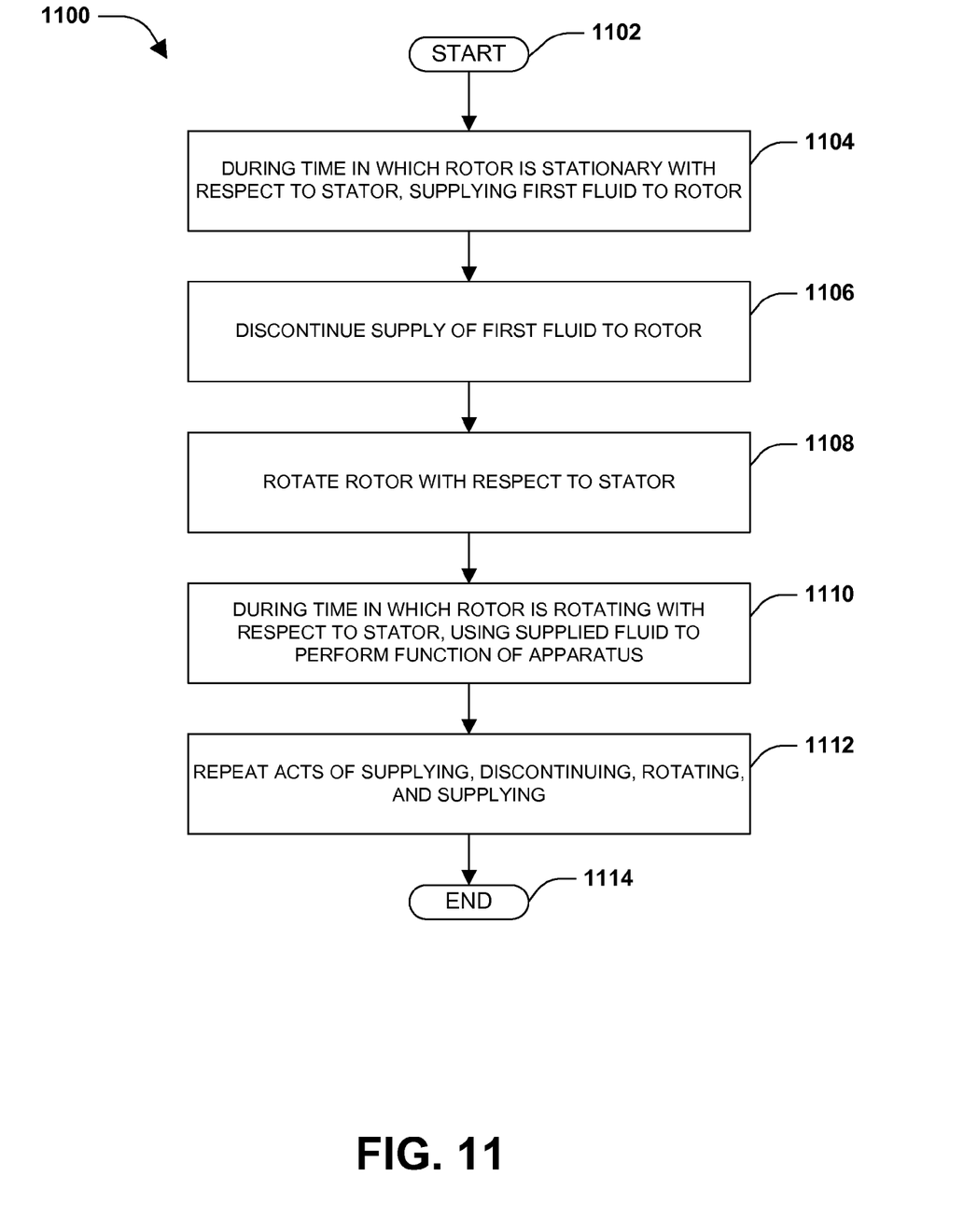
FIG. 11 is a flow chart diagram of an example method for supplying a first fluid to a rotor during a first time the rotor is stationary, discontinuing the supply of the first fluid when the rotor is rotating, and supplying a second fluid to the rotor during a second time in which the rotor is stationary.

A method may be devised for supplying fluid (e.g., gas, compressed gas, liquid, etc.) to a rotor of a radiation treatment apparatus, such that fluid is supplied when the rotor is stationary and not supplied when the rotor is rotating. FIG. 11 is a flow diagram of an example method 1100 for use with a radiation treatment apparatus that includes a stator, a rotor, and a radiation source carried by the rotor for applying an ionization radiation to an object to be treated. The method may be automated and/or manual (e.g., requiring a user's assistance). The example method 1100 begins at 1102 and involves supplying a first batch of fluid to the rotor during a time in which the rotor is stationary with respect to the stator, at 1104. In one example, a quick-connect coupler on the rotor couples to a quick-connect coupler on a fluid passage that is attached to the stator, and the first batch of fluid is supplied to the rotor from the stator. In another example, a removable storage component may be supplied with the first batch of fluid, and connected to the rotor while it is stationary. Further, the first batch of fluid supplied to the rotor may replace a batch of fluid discharged from the rotor. In one example, a valve may be opened to discharge a previous batch of fluid from the rotor, and the first batch of fluid is supplied to the rotor through a quick-connect coupler.

At 1106, the supply of the first batch of fluid to the rotor is discontinued. The supply may be discontinued because the rotor is preparing to rotate and/or a predetermined amount of fluid is in the rotor, for example. If quick-connect couplers, for example, are used to supply the first batch of fluid to the rotor, the supply may be discontinued by uncoupling the quick-connect couplers. It will be appreciated the first batch of fluid's point of entry on the rotor may be sealed when the first batch of fluid is no longer being supplied to the rotor to prevent the first batch of fluid from leaking out of the rotor. If a removable storage component is used to supply the first batch of fluid, the supply of the first batch of fluid to the rotor may be discontinued when the removable storage component is attached to the rotor.

At 1108, the rotor rotates with respect to the stator. For example, in medicine, the radiation treatment apparatus may be a computerized axial tomography (CAT) scanner and the rotor may rotate around an object lying on an object support to provide radiation to multiple views of a tumor.

At 1110, the supplied fluid is used to perform a function of the apparatus during a time in which the rotor is rotating with respect to the stator. For example, the fluid may be used to vary a characteristic, such as a radiation beam's shape, of the ionizing radiation that is applied to the object. The fluid may also be used to cool the radiation source, for example, as it produces radiation.

At 1112, one or more of the acts of supplying, discontinuing, rotating, and supplying may be repeated. A first supply may be used for a predetermined number of rotations, a predetermined amount of time, and/or until the first supply, in the rotor, falls below some predetermined threshold, for example. A detection component on the radiation treatment apparatus, for example, may indicate when to supply a second batch of fluid to the rotor and/or discharge a first batch of fluid from the rotor. Having supplied and resupplied the rotor with fluid, the example method 1100 ends at 1114.

Various operations of embodiments are provided herein. The order in which some or all of the operations are described should not be construed as to imply that these operations are necessarily order dependent. Alternative ordering will be appreciated by one skilled in the art having the benefit of this description. Further, it will be understood that not all operations are necessarily present in each embodiment provided herein.

Moreover, the word "example" is used herein to mean serving as an example, instance, or illustration. Any aspect or design described herein as "example" is not necessarily to be construed as advantageous over other aspects or designs. Rather, use of the word example is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. A radiation treatment apparatus comprising:
   a stationary gantry portion;
   a rotating gantry portion configured to rotate relative to the stationary gantry portion, wherein the rotating gantry portion is configured to receive a supply of fluid during a period in which the rotating gantry portion is stationary relative to the stationary gantry portion and to discontinue receiving the supply of fluid during a second period in which the rotating gantry portion is rotating relative to the stationary gantry portion;

an ionizing radiation source carried by the rotating gantry portion; and a beam shaper configured to use the supply of fluid to vary a shape of a radiation beam emitted by the ionizing radiation source.

2. The apparatus of claim 1, wherein the rotating gantry portion is configured to receive the supply of fluid from the stationary gantry portion.

3. The apparatus of claim 1, wherein the beam shaper is configured to use the supply of fluid to vary the shape of the radiation beam during the second period.

4. The apparatus of claim 1, wherein the supply of fluid comprises a supply of compressed gas and the beam shaper comprises a pneumatic actuator configured to use the compressed gas.

5. The apparatus of claim 1, wherein the rotating gantry portion comprises a storage component configured to store the supply of fluid received during the period.

6. The apparatus of claim 5, wherein the storage component is detachable from the rotating gantry portion.

7. The apparatus of claim 5, wherein the storage component is detached from the rotating gantry portion to receive the supply of fluid during the period.

8. The apparatus of claim 5, wherein the storage component comprises a detection component configured to detect when the supply of fluid is below some threshold.

9. The apparatus of claim 1, further comprising a coupler configured to couple the rotating gantry portion to the stationary gantry portion during the period to facilitate receiving the supply of fluid.

10. The apparatus of claim 9, wherein the coupler is configured to automatically decouple the rotating gantry portion from the stationary gantry portion prior to the second period.

11. The apparatus of claim 9, wherein the coupler is a quick-connect coupler.

12. The apparatus of claim 1, wherein the rotating gantry portion is configured to be placed in a parked position relative to the stationary gantry portion prior to the period.

13. The apparatus of claim 1, wherein the beam shaper is carried by the rotating gantry portion.

14. The apparatus of claim 1, further comprising a cooling component carried by the rotating gantry portion and configured to cool a second supply of fluid.

15. The apparatus of claim 14, the rotating gantry portion comprising a storage component configured to store the second supply of fluid.

16. The apparatus of claim 14, wherein the second supply of fluid is used to cool the ionizing radiation source.

17. The apparatus of claim 1, further comprising a patient support configured to support a human patient in a treatment region during the second period.

18. The apparatus of claim 1, wherein the supply of fluid is stored in a canister that is exchanged between the stationary gantry portion and the rotating gantry portion during the period.

19. The apparatus of claim 1, wherein the supply of fluid comprises a supply of gas.

20. A radiation treatment apparatus comprising:
a stationary gantry portion;
a rotating gantry portion configured to rotate relative to the stationary gantry portion and comprising:
a storage component configured to receive a supply of fluid during a period in which the rotating gantry portion is stationary relative to the stationary gantry portion and to discharge at least a portion of the supply of fluid during a second period in which the rotating gantry portion is rotating relative to the stationary gantry portion;
an ionizing radiation source carried by the rotating gantry portion; and
a beam shaper carried by the rotating gantry portion and configured to use the at least a portion of the supply of fluid to vary a shape of a radiation beam emitted by the ionizing radiation source.

21. The apparatus of claim 20, wherein the storage component is detachable from the rotating gantry portion during the period.

22. The apparatus of claim 20, wherein the stationary gantry portion comprises a retractable mechanism configured to detach the storage component from the rotating gantry portion during the period to facilitate receiving the supply of fluid.

23. The apparatus of claim 20, further comprising a cooling component carried by the rotating gantry portion and configured to cool a second supply of fluid used to cool the ionizing radiation source.

24. The apparatus of claim 23, wherein the rotating gantry portion comprises a second storage component configured to receive the second supply of fluid during the period.

25. The apparatus of claim 23, wherein the supply of fluid comprises a supply of gas and the second supply of fluid comprising a supply of a liquid.

26. The apparatus of claim 20, wherein the beam shaper comprises a pneumatic actuator.

27. A method, comprising:
transferring a supply of fluid from a stationary gantry portion to a rotating gantry portion during a period in which the rotating gantry portion is stationary relative to the stationary gantry portion;
discontinuing the supply of fluid to the rotating gantry portion in preparation for rotation of the rotating gantry portion relative to the stationary gantry portion; and
using the supply of fluid to vary a shape of a radiation beam emitted by an ionizing radiation source during a second period in which the supply of fluid to the rotating gantry portion is discontinued.

28. The method claim 27, wherein the rotating gantry portion is rotated relative to the stationary gantry portion during the second period.

29. The method of claim 27, wherein the transferring comprises:
transferring a storage component comprising the supply of fluid from the stationary gantry portion to the rotating gantry portion during the period.

30. The method of claim 27, further comprising exposing an object to the radiation beam to treat the object.

31. The method of claim 27, wherein the transferring comprises:
coupling a supply line configured to supply the fluid between the stationary gantry portion and the rotating gantry portion.

* * * * *